United States Patent [19]

Goldstein et al.

[11] 4,215,112
[45] Jul. 29, 1980

[54] TRIPEPTIDES AND METHODS

[75] Inventors: Gideon Goldstein, Short Hills; George Heavner, Flemington, both of N.J.

[73] Assignee: Ortho Pharmaceutical Corporation, Raritan, N.J.

[21] Appl. No.: 20,159

[22] Filed: Mar. 14, 1979

[51] Int. Cl.$^2$ ............... A61K 37/00; C07C 103/52
[52] U.S. Cl. ............................. 424/177; 260/112.5 R
[58] Field of Search ............... 260/112.5 R; 424/177

[56] References Cited
U.S. PATENT DOCUMENTS 4,098,777  7/1978  Veber et al. ............... 260/112.5 R Primary Examiner—Delbert R. Phillips
Attorney, Agent, or Firm—Geoffrey G. Dellenbaugh

[57] ABSTRACT

There are disclosed new biological active polypeptides:

A—X—B wherein A is deamino-LYS or LYS; X is a suitable neutral aliphatic amino acid residue; e.g., one selected from the group consisting of SER, ALA, 2-Me-ALA, GLY, LEU, THR, D-SER, D-ALA, D-THR, allo-THR, D-LEU, and SAR; B is GLN-R', decarboxy-GLN, or

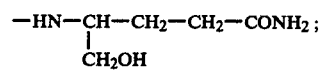

and R' is a substituent which does not substantially affect the biological activity of the tripeptide.

These polypeptides have the capability of inducing the differentiation of T-lymphocytes as measured by the acquisition of the thymic differentiation antigen Th-1, as well as B-lymphocytes as measured by the acquisition of the differentiation antigen Bu-1. The polypeptides are thus useful in thymic function and immunity areas such as in treatment for congenital absence of thymus. Also provided are therapeutic compositions and methods for use of the polypeptides.

16 Claims, No Drawings

TRIPEPTIDES AND METHODS

FIELD OF THE INVENTION

This invention relates generally to new polypeptides, therapeutic compositions containing same, and uses thereof.

DESCRIPTION OF THE PRIOR ART

It is well-known that many polypeptides have been isolated from various tissues and organs (including the blood) of animals. Many of these polypeptides are related to immune function in the body, as, for example, the various immune globulins, the thymic hormone thymopoietin, and the like. Indeed, one of the Applicants has isolated and synthesized several of these polypeptides, as described in, for example, in U.S. Pat. Nos. 4,002,602 and 4,077,949 as well as in several scientific articles.

Until about the past decade, little was known about the thymus, although it is now understood that the thymus is one of the organs principally responsible for immune function in mammals and birds. Despite keen interest in possible functions of the thymus and early speculation and experimentation, little was known of the function of the thymus until recently. It is now realized, however, that the thymus is a compound organ with both epithelial (endocrine) and lymphoid (immunological) components and thus the thymus is involved in the immunity functions of the body. The thymus consists of an epithelial stroma derived from the third branchial arch and lymphocytes derived from stem cells originating in haemopoietic tissues, Goldstein, et al., *The Human Thymus*, Heinemann, London, 1969. Lymphocytes are differentiated within the thymus and leave as mature thymus-derived cells, called T cells, which circulate to the blood, lymph, spleen and lymph nodes. The induction of stem cell differentiation within the thymus appears to be mediated by secretions of the epithelial cells of the thymus.

It has been known for some time that the thymus is connected with the immunity characteristics of the body and, therefore, great interest has been indicated in substances which have been isolated from the thymus. In this regard, there have been published in recent years a relatively large body of articles based on scientific work relating to materials which are present in bovine thymus. In fact, one of the Applicants has published a number of articles which relate to research in this area. Pertinent publications may be found, for example, in *The Lancet*, July 20, 1968, pp. 119–122; *Triangle*, Vol. II, No. 1, pp. 7–14, 1972; *Annals of the New York Academy of Sciences*, Vol. 183, pp. 230–240, 1971; and *Clinical and Experimental Immunology*, Vol. 4, No. 2, pp. 181–189, 1969; *Nature*, Vol. 247, pp. 11–14, 1974; *Proceedings of the National Academy of Sciences USA*, Vol. 71, pp. 1474–1478, 1974; *Cell*, Vol. 5, pp. 361–365 and 367–370, 1975; *Lancet*, Vol. 2, pp. 256–259, 1975; *Proceedings of the National Academy of Sciences USA*, Vol. 72, pp. 11–15, 1975; *Biochemistry*, Vol. 14, pp. 2214–2218, 1974; *Nature*, Vol. 255, pp. 423–424, 1975.

A second class of lymphocytes having immune function are the B lymphocytes or B cells. These are differentiated in the Bursa of Fabricius in birds and by an as-yet-unidentified organ in mammals. T-cells and B-cells cooperate in many aspects of immunity. See, for example, articles by one of the Applicants in *Science*, 193, 319 (July 23, 1976) and *Cold Spring Harbor Symposia on Quantitative Biology*, Vol. XLI, 5 (1977).

A nonapeptide material has recently been isolated from porcine serum by J. F. Bach, et al. and identified as "facteur thymique serique" (FTS). The isolation of this material and its structure are disclosed in *C. R. Acad. Sc. Paris*, t. 283 (Nov. 29, 1976), Series D-1605 and *Nature* 266, 55 (Mar. 3, 1977). The structure of this nonapeptide has been identified as GLX—ALA—LYS—SER—GLN—GLY—GLY—SER—ASN, where "GLX" represents either glutamine or pyroglutamic acid. The material where GLX is glutamine or pyroglutamic acid has been synthesized. In these articles, Bach disclosed that his nonapeptide FTS selectively differentiated T cells (and not B cells) by use of an E rosette assay. Bach, therefore, concluded that his material was a thymic hormone. Recently, a more thorough investigation of the activity of this nonapeptide by one of the present Applicants disclosed and FTS differentiated both T cells and B cells and was, therefore, more like ubiquitin in its activity than thymopoietin. Brand, Gilmour and Goldstein, *Nature*, 269, 597–98 (1977).

One of the Applicants has disclosed in his copending application entitled "New Tetrapeptides and Methods," Ser. No. 960,550, filed Nov. 17, 1978, that the 4-amino acid polypeptide sequences H—ALA—LYS—SER—GLN—OH and H—SAR—LYS—SAR—GLN—NH$_2$ (among others) possess the same activity as FTS.

It has now surprisingly been discovered that a synthesized 3-amino acid polypeptide segment resembling a portion of this FTS nonapeptide possesses many of the characteristics of the nonapeptide discussed in the above publications.

SUMMARY OF THE INVENTION

It is accordingly one object of this invention to provide new polypeptides which are important biologically.

A further object of the invention is to provide new polypeptides which have the ability to induce differentiation of both T-lymphocytes as well as B-lymphocytes and are, therefore, highly useful in the immune systems of humans and animals.

A further object of the invention is to provide methods for synthesizing the novel polypeptides of this invention, as well as compositions and methods for use in biological actions.

Other objects and advantages of the invention will become apparent from an examination of the present disclosure.

In satisfaction of the foregoing objects and advantages, there is provided by this invention the novel biologically active polypeptide having the following amino acid sequence:

$$A—X—B \qquad (I)$$

wherein A is deamino-LYS or LYS; X is a suitable neutral aliphatic amino acid residue; e.g., one selected from the group consisting of SER, ALA, 2-Me-ALA, GLY, LEU, THR, D-SER, D-ALA, D-THR, allo-THR, D-LEU, and SAR; B is GLN-R′, decarboxy-GLN, or

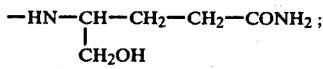

and R' is a member selected from the group consisting of OH, NH$_2$, NHR", N(R")$_2$, OR", GLY, GLY-GLY, GLY-GLY-SER, and GLY-GLY-SER-ASN; and R" is a member selected from the group consisting of C$_1$–C$_7$ alkyl, C$_6$–C$_{12}$ aryl, C$_6$–C$_{20}$ alkaryl, C$_6$–C$_{20}$ aralkyl, C$_2$–C$_7$ alkenyl, and C$_2$–C$_7$ alkynyl.

Also provided is a procedure for preparation of the polypeptides of the invention by solid phase peptide synthesis, as well as therapeutic compositions containing the polypeptides, and methods for administration thereof to humans and animals for effecting biological actions thereon.

DETAILED DESCRIPTION OF THE INVENTION

The subject polypeptides are tripeptides of which the first and third amino acid residue are the same as the third and fifth residue, respectively, of FTS. The second residue is selected from the group described above. While this same sequence of three amino acid residues is found as a portion of certain of the tetrapeptides disclosed in copending application Ser. No. 960,550, filed Nov. 17, 1978, (for X=SAR or SER), it is by no means obvious that the shorter sequence would possess the same activity or indeed any activity at all. It is also highly unusual that the subject tripeptides have a high degree of potency.

It should be understood that the terminal carboxylic acid group is not essential to the biological activity of the tripeptide, as is the case for some polypeptides. It is therefore, considered that the scope of the present invention includes not only those tripeptides of formula (I) wherein R' is OH, but also those which are substituted on the carboxyl terminus by one or more other functional groups which do not substantially affect the biological activity disclosed herein.

From this statement, it will be understood that these functional groups include such normal substitution as amidation on the free carboxylic acid group, as well as the substitution of additional amino acids and polypeptides.

One preferred embodiment of the present invention is the peptide of formula I wherein X is SAR, R' is OH, NH$_2$, NHR", N(R")$_2$ or OR", and R" is C$_1$–C$_7$ alkyl or C$_6$–C$_{12}$ aryl. A second preferred embodiment is the peptide of formula I wherein X is SAR and R' is OH or NH$_2$. A third preferred embodiment is the peptide of formula I wherein A is LYS, X is SAR, and B is GLN-NH$_2$. This preferred embodiment may be symbolized chemically as:

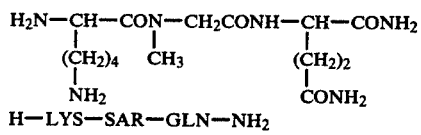

Also included within the scope of the invention are the pharmaceutically acceptable salts of the polypeptides. As acids which are able to form salts with the polypeptides, there may be mentioned inorganic acids such as hydrochloric acid, hydrobromic acid, perchloric acid, nitric acid, thiocyanic acid, sulfuric acid, phosphoric acid, etc. and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid or sulfanilic acid, for instance.

Throughout the present application, the amino acid components of the peptide are identified by abbreviations for convenience. These abbreviations are as follows:

| Amino Acid | Abbreviated Designation |
|---|---|
| L-Alanine | ALA |
| L-Asparagine | ASN |
| L-Serine | SER |
| L-Glutamine | GLN |
| L-Leucine | LEU |
| L-Lysine | LYS |
| L-Threonine | THR |
| Glycine | GLY |
| Sarcosine | SAR |
| D-Alanine | D-ALA |
| D-Serine | D-SER |
| D-Threonine | D-THR |
| D-Leucine | D-LEU |
| allo-Threonine | allo-THR |
| 2-Methylalanine | 2-Me-ALA |

The terms "deamino-LYS" and "decarboxy-GLN" as used herein refer, respectively, to an L-lysine residue in which the α-amino group has been replaced by hydrogen and an L-glutamine residue in which the terminal carboxyl group has been replaced by hydrogen. These two residues have the following respective formulas: H$_2$N—(CH$_2$)$_5$—CO— and —HN—(CH$_2$)$_3$—CONH$_2$.

The tripeptides of this invention have been found to exhibit characteristics similar to the 9-amino acid polypeptide FTS isolated from porcine blood as disclosed in the above-referenced Bach, et al., articles. The peptides of this invention are particularly characterized in their ability to induce the differentiation of T-precursor cells as well as B-precursor cells.

It has been found that the polypeptides of this invention induce the differentiation of immunocyte-precursor cells in vitro in the same way as the nonapeptides disclosed by Bach. Thus, the polypeptides of this invention have been found to induce the differentiation of both T-precursor cells, as measured by the acquisition of the thymic differentiation antigen Th-1, as well as B-precursor cells, as measured by the acquisition of the differentiation antigen Bu-1. Stated another way, the subject polypeptides have the capability of inducing differentiation of both Th-1+ T-lymphocytes and Bu-1+ B-lymphocytes.

To provide an understanding of the importance of the differentiating biological characteristics of the polypeptides of this invention, it should be noted that the function of the thymus in relation to immunity may be broadly stated as the production of thymus-derived cells, or lymphocytes, which are called T cells. T cells form a large proportion of the pool of recirculating small lymphocytes. T cells have immunological specificity and are directly involved in cell-mediated immune responses (such as homograft responses), as effector cells. T cells, however, do not secrete humoral antibodies. These antibodies are secreted by cells (termed B cells) derived directly from the bone marrow independently of the thymic influence. However, for many antigens, B cells require the presence of appropriately reactive T cells before they can produce antibodies. The mechanism of this process of cell cooperation is not yet completely understood.

From this explanation, it may be said that in operational terms, the thymus is necessary for the development of cellular immunity and many humoral antibody responses and it affects these systems by inducing, within the thymus, the differentiation of haemopoietic stem cells to T cells. This inductive influence is mediated by secretions of the epithelial cells of the thymus, that is, the thymic hormones.

Further, to understand the operation of the thymus and the cell system of lymphocytes, and the circulation of lymphocytes in the body, it should be pointed out that stem cells arise in the bone marrow and reach the thymus by the bloodstream. Within the thymus, stem cells become differentiated to immunologically competent T cells, which migrate to the bloodstream and, together with B cells, circulate between the tissues, lymphatics, and the bloodstream.

The cells of the body which secrete antibody (B cells) also develop from haemopoietic stem cells, but their differentiation is not determined by the thymus. In birds, they are differentiated in an organ analogous to the thymus, called the Bursa of Fabricius. In mammals, no equivalent organ has been discovered and it is thought that these cells differentiate within the bone marrow. Hence, they are termed bone marrow-derived cells or B cells. The physiological substances dictating this differentiation remain completely unknown.

As pointed out above, the polypeptides of this invention are therapeutically useful in the treatment of humans and animals. Since the new polypeptides have the capability of inducing the differentiation of lymphopoietic stem cells originating in the haemopoietic tissues to both thymus-derived lymphocytes (T cells) and immunocompetent B cells which are capable of involvement in the immune response of the body, the products of this invention are considered to have multiple therapeutic uses. Primarily, since the compounds have the capability of carrying out certain of the indicated functions of the thymus, they have application in various thymic function and immunity areas. A primary field of application is in the treatment of DiGeorge Syndrome, a condition in which there is a congenital absence of thymus. Injection of one of the subject polypeptides, as further set out below, will overcome this deficiency. Another application is in agammaglobulinemia, which is due to a defect of the putative B cell differentiative hormone of the body. Injection of one of the subject polypeptides will overcome this defect. Since the subject polypeptides are extremely active at low concentrations, they are useful in augmenting the collective immunity of the body in that they increase therapeutic stimulation of cellular immunity and humoral immunity and are thereby useful in the treatment of diseases involving chronic infection in vivo, such as fungal or mycoplasma infections, tuberculoses, leprosy, acute and chronic viral infections, and the like. Further, the subject peptides are considered to be useful in any area in which cellular or humoral immunity is an issue and particularly where there are deficiencies in immunity such as in the DiGeorge Syndrome mentioned above. Further, because of the characteristics of the polypeptides, they have in vitro usefulness in inducing the development of surface antigens of T cells, in inducing the development of the functional capacity to achieve responsiveness to mitogens and antigens, and cell collaborativity in enhancing the ability of B cells to produce antibodies. They have in vitro usefulness in inducing the development of B cells as measured by the development of surface receptors for complement. The subject peptides are also useful in inhibiting the uncontrolled proliferation of lymphocytes which are responsive to ubiquitin (described in U.S. Pat. No. 4,002,602). An important characteristic of the subject polypeptides is their in vivo ability to restore cells with the characteristics of T cells and also their in vivo ability to restore cells with the characteristics of B cells. They are, therefore, useful in the treatment of relative or absolute B cells deficiencies as well as relative or absolute T cells deficiencies, whether or not these deficiencies are due to deficiencies in the tissue differentiating B cells or the thymus, respectively, or to some other cause.

A further important property of the polypeptides of this invention is that they are highly active in very low concentrations. Thus, it has been found that the subject polypeptides are generally active in concentrations of about 1 ng/ml, while one preferred polypeptide (H—LYS—SAR—GLN—NH$_2$) is active in concentrations ranging from about 100 pg/ml. The carrier may be any of the well-known carriers for this purpose including normal saline solutions, preferably with a protein diluent such as bovine serum albumin to prevent adsorptive losses to glassware at these low concentrations. The polypeptides of this invention are generally active when parenterally administered at a range of above about 1 $\mu$g/kg of body weight. For the treatment of DiGeorge Syndrome, the polypeptides may be parenterally administered at a rate of about 1 to about 100 $\mu$g/kg of body weight. Generally, the same range of dosage amounts may be used in treatment of the other conditions or diseases mentioned.

To prepare the pharmaceutical compositions of the present invention, a polypeptide of formula (I) possessing pharmacological activity or an acid addition salt thereof is combined as the active ingredient in intimate admixture with a pharmaceutical carrier according to conventional pharmaceutical compounding techniques, which carrier may take a wide variety of forms depending on the form of preparation desired for administration, e.g., sublingual, rectal, nasal, oral, or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixiers, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. While these compositions have been illustrated above by those designed for parenteral administration, which is preferred, oral compositions are also clearly contemplated. For oral administration, the polypeptide concentration should generally be about one hundred to one thousand times greater (in mg/kg body weight) than for parenteral administration, e.g., from about 100 µg/kg to about 20 mg/kg body weight.

The polypeptides of this invention were prepared using the concepts similar to those described by Merrifield as reported in *Journal of American Chemical Society*, 85, pp 2149-2154, 1963. The synthesis involved the stepwise addition of protected amino acids to a growing peptide chain which was bound by covalent bonds to a solid resin particle. By this procedure, reagents and by-products were removed by filtration and the purification of intermediates were eliminated. The general concept of this method depends on attachment of the C-terminal amino acid of the chain to a solid polymer by a covalent bond and the addition of the succeeding amino acids one at a time in a stepwise manner until the desired sequence is assembled. Finally, the peptide is removed from the solid support and protective groups removed. This method provides a growing peptide chain attached to a completely insoluble solid particle so that it is in a convenient form to be filtered and washed free of reagents and by-products.

The amino acids may be attached to any suitable polymer which merely has to be readily separable from the unreacted reagents. The polymer may be insoluble in the solvents used or may be soluble in certain solvents and insoluble in others. The polymer should have a stable physical form permitting ready filtration. It must contain a functional group to which the first protected amino acid can be firmly linked by a covalent bond. Various insoluble polymers suitable for this purpose are those such as cellulose, polyvinyl alcohol, polymethacrylate and sulfonated polystyrene but in the synthesis of this invention, there was generally used a chloromethylated copolymer of styrene and divinylbenzene. Polymers which are soluble in organic solvents while being insoluble in aqueous solvents may also be used. One such polymer is a polyethylene glycol having a molecular weight of about 20,000, which is soluble in methylene chloride but insoluble in water. The use of this polymer in peptide synthesis is described in F. Bayer and M. Mutter, *Nature* 237, 512 (1972) and references contained therein.

The various functional groups on the amino acid which were active, but which were not to enter into the reactions, were protected by conventional protecting groups as used in the polypeptide art throughout the reaction. Thus, the functional group on lysine was protected by protecting groups which could be removed on completion of the sequence without adversely affecting the polypeptide final product. In the synthesis, the ninhydrin test was used to determine if coupling was complete. If complete coupling was not indicated, the coupling was repeated with the same protected amino acid before deprotection.

The C-terminal amino acid may be attached to the polymer in a variety of well-known ways. Summaries of methods for attachment to halomethyl resins are given in Horiki, et al., *Chem. Letters*, pp. 165-168 (1978) and Gisin, *Helv. Chim. Acta*, 56, 1476 (1973), and references given therein. If a C-terminal amide is to be prepared, one of two routes may be employed. Either the peptide resin prepared according to the Merrifield technique may be cleaved using anhydrous ammonia, or a benzhydrylamine resin may be employed. Cleavage from this latter resin with hydrogen fluoride affords the C-terminal amide peptide. The use of a benzhydrylamine resin is shown in, for example, J. Rivier, et al., *J. Med. Chem.*, 16, 545-549 (1973).

The general procedure for preparation of C-terminal carboxyl peptides involved initially esterifying L-glutamine, protected on its amino groups, to the chloromethyl resin by the $CsHCO_3$ method (e.g., as disclosed in the above-referenced Gisin article). The protecting group on the α-amino group of the glutamine amino acid (e.g., t-BOC, i.e., t-butyloxycarbonyl), was then removed without affecting other protecting groups. The coupled amino acid resin was then filtered, washed, and neutralized. The resulting coupled amino acid resin, having the free amino group, was then reacted with a protected sarcosine, preferably alpha-t-BOC-sarcosine, to couple the sarcosine. A suitable coupling agent such as dicyclohexylcarbodiimide may be used. The reactions were then repeated with protected L-lysine until the complete molecule was prepared. The sequence of reactions was carried out as follows:

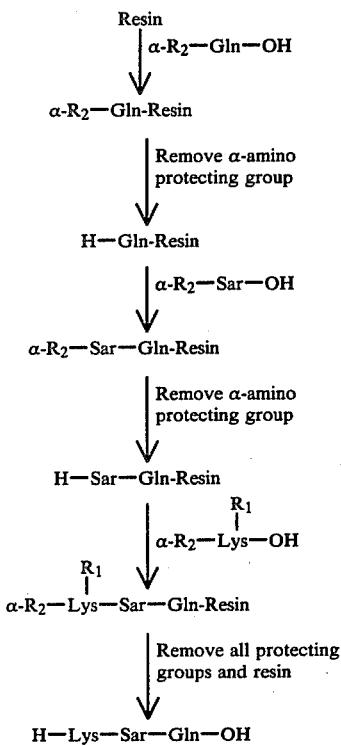

In the above sequence of reactions $R_1$ is a protecting group on the reactive side chain of the lysine amino acid which is not affected or removed when the protective group on the α-amino group is removed to permit further reaction, and $R_2$ is a protecting group of the α-amino group. Preferably, in the above intermediate tripeptide resin, the term $R_1$ stands for a protective grouping such as 2,6-dichlorobenzyloxycarbonyl and $R_2$ stands for t-butyloxycarbonyl. The resin is any of the resins mentioned above as being useful in the process.

After the final intermediate was prepared, the peptide resin was cleaved to remove the $R_1$ and $R_2$ protecting groups thereon and the resin. The protecting groups and resin were removed by conventional means, e.g., by treatment with anhydrous hydrogen fluoride, and the resulting free peptide was then recovered.

As pointed out above, in conducting the process, it is necessary to protect or block the amino groups in order to control the reaction and obtain the products desired. Suitable amino protecting groups which may be usefully employed include salt formation for protecting strongly-basic amino groups, or urethane protecting substitutes such as 4-methoxybenzyloxycarbonyl and t-butyloxycarbonyl. It is preferred to utilize t-butyloxycarbonyl (BOC) or t-amyloxycarbonyl (AOC) for protecting the α-amino group in the amino acids undergoing reaction at the carboxyl end of the molecule, since the BOC and AOC (t-amyloxycarbonyl) protecting groups are readily removed following such reaction and prior to the subsequent step (wherein such α-amino group itself undergoes reaction) by relatively mild action of acids (e.g., trifluoroacetic acid), which treatment does not otherwise affect groups used to protect other reactive side chains. It will thus be understood that the α-amino groups may be protected by reaction with any material which will protect the amino groups for the subsequent reaction(s) but which may later be removed under conditions which will not otherwise affect the molecule. Illustrative of such materials are organic carboxylic or carbonic acid derivatives which will acylate the amino group.

In general, any of the amino groups can be protected by reaction with a compound containing a grouping of the formula:

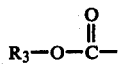

wherein $R_3$ is any grouping which will prevent the amino group from entering into subsequent coupling reactions and which can be removed without destruction of the molecule. Thus, $R_3$ is a straight or branched chain alkyl which may be unsaturated, preferably of 1 to 10 carbon atoms and preferably halo- or cyano-substituted; aryl, preferably of 6 to 15 carbons; cycloalkyl, preferably of 5 to 8 carbon atoms; aralkyl, preferably of 7 to 18 carbon atoms; alkaryl, preferably of 7 to 18 carbon atoms; or heterocyclic, e.g., isonicotinyl. The aryl, aralkyl and alkaryl moieties may also be further substituted as by one or more alkyl groups of 1 to about 4 carbon atoms. Preferred groupings for $R_3$ include t-butyl, t-amyl, tolyl, xylyl and benzyl. Highly preferred specific amino-protecting groups include benzyloxycarbonyl; substituted benzyloxycarbonyl wherein the phenyl ring is substituted by one or more halogens, e.g., Cl or Br, nitro, loweralkoxy, e.g., methoxy, or loweralkyl; t-butyloxycarbonyl, t-amyloxycarbonyl; cyclohexyloxycarbonyl, vinyloxycarbonyl; adamantyloxycarbonyl; biphenylisopropoxycarbonyl; and the like. Other protecting groups which can be used include isonicotinyloxycarbonyl, phthaloyl, p-tolylsulfonyl, formyl and the like.

In conducting the general process of the invention, the peptide is built by reaction of the free α-amino group with a compound possessing protected amino groups. For reaction or coupling, the compound being attached is activated at its carboxyl group so that the carboxyl group can then react with the free α-amino group on the attached peptide chain. To achieve activation the carboxyl group can be converted to any reactive group such as an ester, anhydride, azide, acid chloride, or the like. Alternately, a suitable coupling reagent may be added during the reaction. Suitable coupling reagents are disclosed, e.g., in Bodanszky, et al.—*Peptide Synthesis*, Interscience, second edition, 1976, chapter five, including carbodiimides (e.g., dicyclohexylcarbodiimide), carbonyldiimidizole, and the like.

It should also be understood that during these reactions, the amino acid moieties contain both amino groups and carboxyl groups and usually one grouping enters into the reaction while the other is protected. Prior to the coupling step, the protecting group on the alpha or terminal amino group of the attached peptide is removed under conditions which will not substantially affect other protecting groups, e.g., the group on the epsilon-amino of the lysine molecule. The preferred procedure for effecting this step is mild acidolysis, as by reaction at room temperature with trifluoroacetic acid.

As may be appreciated, the above-described series of process steps results in the production of the tripeptide of formula (II) as follows:

  (II)

The substituted tripeptide of formula (II) wherein the carboxyl terminal may be further substituted as described above, may then be prepared by reaction of the tripeptide of formula (II) or the protected peptide resin with suitable reagents to prepare the desired derivatives. Reactions of this type such as esterification, amidation, and the like, are, of course, well-known in the art. Further, other amino acids, that is amino acid groups which do not affect the biological activity of the tripeptide sequence, may be added to the carboxyl end of the peptide chain by the same sequence of reactions by which the tripeptide itself was synthesized. Still further, substitution of another desired amino acid residue for sarcosyl may be accomplished by employing the desired substituent (suitably protected) in place of sarcosine in the preceding sequence of reactions by which the unsubstituted tripeptide was synthesized.

The corresponding C-terminal amide peptides may also be prepared as described above but substituting a benzhydrylamine resin for the chloromethyl resin used therein.

To prepare the corresponding deamino lysine peptides, the above-discussed synthetic technique is followed but substituting an equivalent amount of suitably protected deamino lysine for the protected lysine used therein.

The corresponding peptides wherein B is decarboxy-GLN or —HN—CH(CH₂OH)—CH₂CH₂—CONH₂ may be prepared by a slight modification of the above-described solid phase synthesis. The appropriate L-glutamic acid derivative [H₂N—(CH₂)₃—COOH or H₂N—CH(CH₂OH)—CH₂CH₂COOH] is attached to the resin substrate via its γ carboxy group by means of a benzhydryl amine group, the remainder of the desired sequence is coupled as described above, the protecting groups are removed, and the resulting peptide is cleaved from the resin by means of hydrogen fluoride to yield a peptide having a terminal decarboxy-glutamine or L-glutaminol residue, respectively.

While the solid phase technique of Merrifield has been used to prepare the subject polypeptides, it is clearly contemplated that classical techniques described in, for example, M. Bodanszky, et al., *Peptide Synthesis*, Interscience, second edition, 1976, may also be employed.

The purity and identity of the subject peptides were determined by well-known methods such as, for example, thin layer chromatography, electrophoresis, amino acid analysis, and the like.

The following Examples are presented to illustrate the invention, but it is not to be considered as limited thereto. In the Examples, and throughout the specification, parts are by weight unless otherwise indicated.

EXAMPLE I

In preparation of the polypeptide of this invention, the following materials were purchased commercially:
Alpha-BOC-L-Glutamine
Alpha-BOC-ε-2-chlorobenzyloxycarbonyl-L-lysine
Alpha-BOC-Sarcosine In these reagents, BOC is t-butyloxycarbonyl. "Sequenal" grade reagents for amino acid sequence determinations, dicyclohexyl carbodiimide, ninhydrin, and the resin were purchased commercially. The resin used was a polystyrene divinyl benzene resin, 200–400 mesh size containing 1% divinyl benzene and 0.75 mM of chloride per gram of resin.

In preparation of the polypeptide, α-BOC-L-Glutamine was esterified to chloromethylated resin by the CsHCO$_3$ method of Gisin referred to above. The resulting α-BOC-L-Glutamine-resin contained 0.4–0.5 millimole of amino acid per gram of resin. Using a Schwarz-/Mann Automatic Peptide Synthesizer, the following program was used to couple each protected amino acid to the α-BOC-amino acid resin:

1. Prewashing with 40% trifluoroacetic acid (TFA) in CH$_2$Cl$_2$, once, 1.5 min.
2. Deprotection with 40% TFA in CH$_2$Cl$_2$, once, 20 min.
3. Washing with CHCl$_3$, once, 1.5 min.
4. Washing with EtOH, once, 1.5 min.
5. Washing with CH$_2$Cl$_2$, twice, 1.5 min.
6. Prewashing with 10% Et$_3$N in CH$_2$Cl$_2$, once, 1.5 min.
7. Neutralization with 10% Et$_3$N in CH$_2$Cl$_2$, once, 10 min.
8. Washing with CH$_2$Cl$_2$, three times, 1.5 min.
9. Addition of BOC-protected amino acid (5 molar excess) in dimethylformamide (DMF) and CH$_2$Cl$_2$ (1:9 vol./vol.)
10. Addition of DCC in CH$_2$Cl$_2$ (0.5 M 5 molar excess), the reaction time was up to 2 hours
11. Washing with CH$_2$Cl$_2$, twice, 1.5 min.

Thereafter, the other α-BOC-amino acids were similarly coupled to the deprotected α-amino group of the peptide-resin in the correct sequence to result in the polypeptide of this invntion using equivalent amounts of dicyclohexylcarbodiimide. After each coupling reaction, an aliquot of resin was tested with ninhydrin and if a positive test resulted, coupling was taken to be incomplete and was repeated with the same protective amino acid. As a result of the several coupling reactions, the intermediate tripeptide-resin was prepared.

This peptide-resin was cleaved and the protective groups removed in a Kel-F cleavage apparatus (Peninsula Laboratories, Inc.) using 10 ml anhydrous hydrogen fluoride per gram of resin at 0° C. for 60 minutes with 5 ml anisole per gram peptide-resin as scavenger. After evaporation in vacuo to dryness, the residue was washed with anhydrous ether. The crude peptide was dissolved in 10% aqueous acetic acid and filtered. The resin was also washed with 10% aqueous acetic acid, and the combined filtrates were collected and lyophilized to give crude peptide. The crude peptide was purified by countercurrent distribution using n-butanol-:acetic acid:water (4:1:5) as the partition phase to afford the pure peptide. The resulting polypeptide was determined to have the following sequence:

H—LYS—SAR—GLN—OH

The above method was repeated but using a benzhydrylamine resin, substituting α-BOC-L-glutamine-O-nitrophenyl ester for the α-BOC-L-glutamine, and coupling this ester to the resin without use of DCC to prepare the following tripeptide amide:

H—LYS—SAR—GLN—NH$_2$

For identification of the tripeptide amide, thin layer chromatography and electrophoresis were employed. The amino acid composition was determined using an amino acid analyzer. Thin layer chromatography was performed on 20 μg samples on silica gel (Kieselgel, 5×20 cm) using 1:1:1:1 n-butanol:acetic acid:ethyl acetate:water as eluent ($R_f^1$) and on cellulose 6064 (Eastman, 20 × 20 cm) using 15:10:3:12 n-butanol: pyridine:acetic acid:water as eluent ($R_f^2$). The $R_f$ values relative to H—ARG—LYS—AS-P—VAL—TYR—OH were $R_f^1=0.50$ and $R_f^2=0.58$. Ninhydrin was used as a spray reagent. Electrophoresis was performed on a 100 μg sample on Whitman No. 3 paper (5.7×55 cm) using pH 5.6 pyridine-acetate buffer at a voltage of 1000 V for 1.0 hour. The peptide amide had a mobility of 1.93 toward the cathode relative to H—ARG—LYS—ASP—VAL—TYR—OH. Ninhydrin was used as a spray reagent. The peptide amide was 98% pure based on electrophoresis.

EXAMPLE II

To determine the activity and characteristics of the tripeptide amide produced in Example I, the following chicken induction assay was employed. This assay is described in greater detail in Brand, et al., Science, 193, 319–321 (July 23, 1976) and references contained therein.

Bone marrow from newly-hatched chickens was selected as a source of inducible cells because it lacks an appreciable number of Bu-1+ or Th-1+ cells. Pooled cells from femur and tibiotarsus of five newly-hatched chicks of strain SC (Hy-Line) were fractionated by ultracentrifugation on a five-layer discontinuous bovine serum albumin (BSA) gradient. Cells from the two lighter layers were combined, washed, and suspended for incubation at a concentration of 5×10$^6$ cells per milliliter with the appropriate concentration of test polypeptide in RPMI 1630 medium supplemented with 15 mM hepes, 5 percent γ-globulin-free fetal calf serum, deoxyribonuclease (14 to 18 unit/ml), heparin (5 unit/ml), penicillin (100 unit/ml), and streptomycin (100 μg/ml). Controls were incubated with BSA (1 μg/ml) or medium alone. After incubation, the cells were tested in the cytotoxicity assay using chicken Cl and guinea pig C2 to C9 complement fractions as described in the reference article. The proportion of Bu-1+ or Th-1+ cells in each layer was calculated as a cytotoxicity index, 100 (a−b)/a, where a and b are the percentages of viable cells in the complement control and test preparation, respectively. The percentage of cells induced was obtained by subtracting the mean values in the control incubations without inducing agents (usually 1 to 3 percent) from those of the test inductions.

The specificity of the action of the test polypeptide and its similarity to ubiquitin were demonstrated by the inhibition of induction of Bu-1+ B cells and Th-1+ T cells by the test polypeptide upon addition of ubiquitin in a concentration of 100 µg/ml. This high dose of ubiquitin inactivates the ubiquitin receptors and thus prevents the induction of cells by any agent which acts through these receptors.

As a result of this assay, it was discovered that the amidated tripeptide of Example I displayed biological activity similar to that of ubiquitin in inducing the differentiation of both Th-1+ T and Bu-1+ B lymphocytes in a concentration of 100 pg/ml.

EXAMPLE III

Following the procedure of Example I, but substituting an equivalent amount of D-alanine for the sarcosine used therein, there are produced:

H—LYS—D—ALA—GLN—OH

H—LYS—D—ALA—GLN—NH$_2$

EXAMPLE IV

The assay of Example II was repeated, using as the test polypeptide H—LYS—D—ALA—GLN—NH$_2$ produced in Example III. Biological activity similar to that of ubiquitin was observed.

EXAMPLE V

The protected tripeptide chloromethyl resins prepared in Examples I and III are each reacted with an excess of methyl alcohol under transesterification conditions. The protecting groups are then removed and the products are isolated and purified to yield the following peptide esters:

H—LYS—SAR—GLN—OCH$_3$

H—LYS—D—ALA—GLN—OCH$_3$

EXAMPLE VI

The protected tripeptide chloromethyl resins prepared in Examples I and III are each cleaved from the resin using an excess of diethylamine. The protecting groups are removed and the products are isolated and purified to yield the following peptide amides:

H—LYS—SAR—GLN—N(C$_2$H$_5$)$_2$

H—LYS—D—ALA—GLN—N(C$_2$H$_5$)$_2$

EXAMPLES VII-X

Using the reaction techniques described hereinabove for the lengthening of the polypeptide chain, the following polypeptides are prepared which contain the active amino acid sequence but which are substituted on the terminal carboxylic groups by R' to provide the polypeptides of formula:

A—SAR—GLN—R' which is substituted by the amino acids given in the following Table as indicated.

| EXAMPLE NUMBER | A | R' |
|---|---|---|
| VII | deamino-LYS | GLY |
| VIII | LYS | GLY—GLY |
| IX | LYS | GLY—GLY—SER |
| X | LYS | GLY—GLY—SER—ASN |

EXAMPLES XI-XVI

Using the reaction techniques described in Example I but substituting an equivalent amount of the appropriate suitably protected amino acid for the sarcosine or L-lysine used therein, there are produced.

A—X—GLN—OH

| EXAMPLE | A | X |
|---|---|---|
| XI | LYS | SER |
| XII | LYS | THR |
| XIII | deamino-LYS | LEU |
| XIV | deamino-LYS | D-SER |
| XV | LYS | D-THR |
| XVI | LYS | D-LEU |
| XVII | deamino-LYS | allo-THR |

EXAMPLES XVIII-XIX

Using the reaction techniques described in Example I, but substituting for the L-glutamine used therein an equivalent amount of the appropriate L-glutamic acid derivative and attaching it to the resin via its gamma carboxyl group by means of a benzhydryl amine group, there are prepared the following peptides:

| EXAMPLE | PEPTIDE |
|---|---|
| XVIII | H—LYS—SAR—(decarboxy GLN) |
| XIX | H—LYS—SAR—HN—CH—CH$_2$—CH$_2$—CONH$_2$<br>　　　　　　　　　｜<br>　　　　　　　　CH$_2$OH |

EXAMPLES XX-XXIV

Following the procedure of Example I but substituting for the sarcosine used therein an equivalent amount of a suitably protected amino acid, there are produced the following:

| EXAMPLE | PEPTIDE |
|---|---|
| XX | H—LYS—SER—GLN—NH$_2$ |
| XXI | H—LYS—LEU—GLN—OH |
| XXII | H—LYS—D—THR—GLN—NH$_2$ |
| XXIII | H—LYS—D—LEU—GLN—NH$_2$ |
| XXIV | H—LYS—GLY—GLN—NH$_2$ |

The polypeptide derivatives prepared in Examples V-XXIV retain the biological activity as described herein for the active polypeptide segment.

The invention has been described herein with reference to certain preferred embodiments. However, as obvious variations will appear to those skilled in the art, the invention is not to be considered as limited thereto.

What is claimed is:

1. A polypeptide having the capability of inducing the differentiation of both Th-1+ T-lymphocytes and Bu-1+ B-lymphocytes, said polypeptide having the formula:

A—X—B wherein A is deamino-LYS or LYS; X is a suitable neutral aliphatic amino acid residue selected from the group consisting of SER, ALA, 2-Me-ALA, GLY, LEU, THR, D-SER, D-ALA, D-THR, allo-THR, D-LEU, and SAR; B is GLN-R', decarboxy-GLN, or

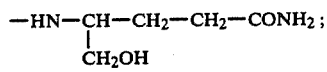

R' is a member selected from the group consisting of OH, $NH_2$, NHR″, N(R″)$_2$, OR″, GLY, GLY—GLY, GLY—GLY—SER, and GLY—GLY—SER—ASN; and R″ is a member selected from the group consisting of $C_1$-$C_7$ alkyl, $C_6$-$C_{12}$ aryl, $C_6$-$C_{20}$ alkaryl, $C_6$-$C_{20}$ aralkyl, $C_2$-$C_7$ alkenyl, and $C_2$-$C_7$ alkynyl; and the pharmaceutically acceptable salts thereof.

2. A polypeptide according to claim 1, having the formula:

A—SAR—B wherein A is deamino-LYS or LYS; B is GLN-R', decarboxy-GLN, or

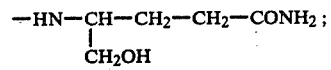

R' is a member selected from the group consisting of OH, $NH_2$, NHR″, N(R″)$_2$, and OR″; and R″ is a member selected from the group consisting of $C_1$-$C_7$ alkyl and $C_6$-$C_{12}$ aryl; and the pharmaceutically acceptable salts thereof.

3. A polypeptide according to claim 1, having the formula:

A—SAR—B wherein A is deamino-LYS or LYS; B is GLN-R', decarboxy-GLN, or

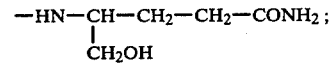

and R' is a member selected from the group consisting of OH and $NH_2$; and the pharmaceutically acceptable salts thereof.

4. A polypeptide of the following sequence:

H—LYS—SAR—GLN—$NH_2$ and the pharmaceutically acceptable salts thereof.

5. A polypeptide of the following sequence:

Deamino-LYS—SAR—GLN—$NH_2$ and the pharmaceutically acceptable salts thereof.

6. A polypeptide of the following sequence:

H—LYS—SAR—GLN—OH and the pharmaceutically acceptable salts thereof.

7. A polypeptide of the following sequence:

Deamino—LYS—SAR—GLN—OH and the pharmaceutically acceptable salts thereof.

8. A therapeutic composition of matter comprising a therapeutically effective amount of the polypeptide of claim 1 in a pharmaceutically acceptable carrier.

9. A therapeutic composition of matter for parenteral administration according to claim 8, wherein the therapeutically effective amount of the polypeptide ranges from about 1 to about 100 μg/kg body weight.

10. A therapeutic composition of matter for oral administration according to claim 8, wherein the therapeutically effective amount of the polypeptide ranges from about 100 μg/kg to about 10 mg/kg body weight.

11. A method for the treatment of conditions resulting from relative or absolute T cell deficiencies which comprises administration of a therapeutically effective amount of the polypeptide of claim 1.

12. A method for the treatment of conditions resulting from relative or absolute B cell deficiencies which comprises administration of a therapeutically effective amount of the polypeptide of claim 1.

13. A method for inducing bone marrow cells to develop the characteristics of thymus-derived lymphocytes which comprises administration of a therapeutically effective amount of the polypeptide of claim 1.

14. A method for inducing bone marrow cells to develop the characteristics of immunocompetent B cells which comprises administration of a therapeutically effective amount of the polypeptide of claim 1.

15. A method for affecting the immune response in the body to assist in the correction of relative or absolute deficiencies of the thymus which comprises administration of a therapeutically effective amount of the polypeptide of claim 1.

16. A method for affecting the immune response in the body to assist in the correction of relative or absolute deficiencies of the body tissues which differentiate B cells which comprises administration of a therapeutically effective amount of the polypeptide of claim 1.

* * * * *